(12) United States Patent
Nakamura (10) Patent No.: US 10,122,991 B2
(45) Date of Patent: Nov. 6, 2018

(54) SURGICAL STEREOSCOPIC OBSERVATION APPARATUS

(71) Applicant: MITAKA KOHKI CO., LTD., Tokyo (JP)

(72) Inventor: Katsuyuki Nakamura, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 183 days.

(21) Appl. No.: 15/229,375

(22) Filed: Aug. 5, 2016

(65) Prior Publication Data

US 2017/0048512 A1 Feb. 16, 2017

(30) Foreign Application Priority Data

Aug. 11, 2015 (JP) ................. 2015-158686
Nov. 11, 2015 (JP) ................. 2015/220895

(51) Int. Cl.

| H04N 13/254 | (2018.01) |
|---|---|
| H04N 13/243 | (2018.01) |
| G02B 21/36 | (2006.01) |
| H04N 13/296 | (2018.01) |
| A61B 90/20 | (2016.01) |
| G02B 21/00 | (2006.01) |

(52) U.S. Cl.
CPC .......... *H04N 13/254* (2018.05); *A61B 90/20* (2016.02); *G02B 21/0012* (2013.01); *G02B 21/361* (2013.01); *G02B 21/368* (2013.01); *H04N 13/243* (2018.05); *H04N 13/296* (2018.05)

(58) Field of Classification Search
CPC .......... H04N 13/0253; H04N 13/0242; H04N 13/00296; G02B 21/0012; A61B 90/20
USPC ............................................ 348/46
See application file for complete search history.

(56) References Cited

U.S. PATENT DOCUMENTS

| 9,375,837 | B2 | 6/2016 | Nakamura | |
|---|---|---|---|---|
| 2007/0058249 | A1* | 3/2007 | Hirose | A61B 1/00193 359/464 |
| 2007/0096038 | A1* | 5/2007 | Tsai | B82Y 15/00 250/458.1 |
| 2012/0229605 | A1* | 9/2012 | Pretorius | G02B 21/0012 348/46 |
| 2014/0005484 | A1* | 1/2014 | Charles | A61B 17/02 600/201 |

(Continued)

FOREIGN PATENT DOCUMENTS

JP 11-318936 11/1999

OTHER PUBLICATIONS

U.S. Appl. No. 15/172,748 to Nakamura, filed Jun. 3, 2016.

*Primary Examiner* — Marnie A Matt
(74) *Attorney, Agent, or Firm* — Greenblum & Bernstein, P.L.C.

(57) ABSTRACT

A surgical stereoscopic observation apparatus has a pair of main optical paths A and a pair of secondary optical paths B, an aligning direction of the paths B differing by 90 degrees from that of the paths A. The main and secondary optical paths involve imaging elements D1 and D2, respectively. This apparatus is able to provide not only electronic images oriented for a main operator and an assistant positioned opposite to the main operator but also electronic images orientated for an assistant positioned on the left or right side of the main operator, thereby allowing the main operator and assistants to cooperatively conduct an operation.

4 Claims, 8 Drawing Sheets

(56) References Cited

U.S. PATENT DOCUMENTS

| | | | |
|---|---|---|---|
| 2014/0055850 A1 | 2/2014 | Doi et al. | |
| 2014/0163320 A1* | 6/2014 | McDowall | A61B 1/00009 600/111 |
| 2014/0211304 A1 | 7/2014 | Nakamura et al. | |
| 2015/0018622 A1* | 1/2015 | Tesar | A61B 1/05 600/202 |
| 2015/0301326 A1 | 10/2015 | Doi et al. | |

* cited by examiner

SURGICAL STEREOSCOPIC OBSERVATION APPARATUS

BACKGROUND OF THE INVENTION

1. Field of the Invention

The present invention relates to a surgical stereoscopic observation apparatus.

2. Description of Related Art

A known surgical stereoscopic observation apparatus has a stand, a camera that is movably supported with the stand and photographs a pair of stereoscopically viewable electronic images having binocular parallax, and a display unit to display the photographed images. The displayed images are stereoscopically observed with the use of a pair of 3D glasses. Instead of displaying the photographed electronic images on the display unit, there is a technique of displaying the images on a pair of left and right display panels incorporated in a 3D viewer, so that an observer may stereoscopically observe the displayed images through eyepieces of the 3D viewer. A related art is disclosed in, for example, Japanese Unexamined Patent Application Publication No. H11-318936.

SUMMARY OF THE INVENTION

The related art mentioned above has, however, only a pair of left and right imaging elements to provide 3D electronic images oriented only for a main operator. These images may electronically be inverted front-rear-wise and left-right-wise to provide 3D electronic images that are oriented for an assistant positioned opposite to the main operator. In some cases, there is a need of positioning an assistant on the left or right side of the main operator, to face the main operator at an angle of 90 degrees. The related art is unable to satisfy such a need, i.e., unable to provide 3D electronic images oriented for the assistant on the left or right side of the main operator.

In consideration of the problem of the related art, the present invention provides a surgical stereoscopic observation apparatus capable of supplying 3D electronic images oriented for an assistant who faces a main operator at an angle of 90 degrees.

According to a first aspect of the present invention, the surgical stereoscopic observation apparatus includes a camera and an electronic image display unit. The camera includes two main optical paths that are defined within the range of light passed through an objective optical system, to guide a pair of first beams from the objective optical system to a pair of first imaging elements through a pair of first variable power optical systems, respectively, and two secondary optical paths that are defined within the range of light passed through the objective optical system and are aligned in a direction differing by 90 degrees from an aligning direction of the main optical paths, to guide a pair of second beams from the objective optical system to a pair of second imaging elements through a pair of second variable power optical systems, respectively. The electronic image display unit displays electronic images which are taken by the camera and have their respective orientations that differ from one another by 90 degrees.

According to a second aspect of the present invention, the camera also includes an illuminating unit.

According to a third aspect of the present invention, the camera includes two focusing beam emitters that emit focusing beams, respectively, toward the objective optical system in parallel with an optical axis of the objective optical system, the two focusing beams converging at a point of focal length of the objective optical system.

According to a fourth aspect of the present invention, the two focusing beams enter the objective optical system at locations that are different from locations where the pairs of the first and second beams for the first and second variable power optical systems exit from the objective optical system.

DESCRIPTION OF PREFERRED EMBODIMENTS

A surgical stereoscopic observation apparatus according to an embodiment of the present invention will be explained with reference to FIGS. 1 to 8.

Figure 1:
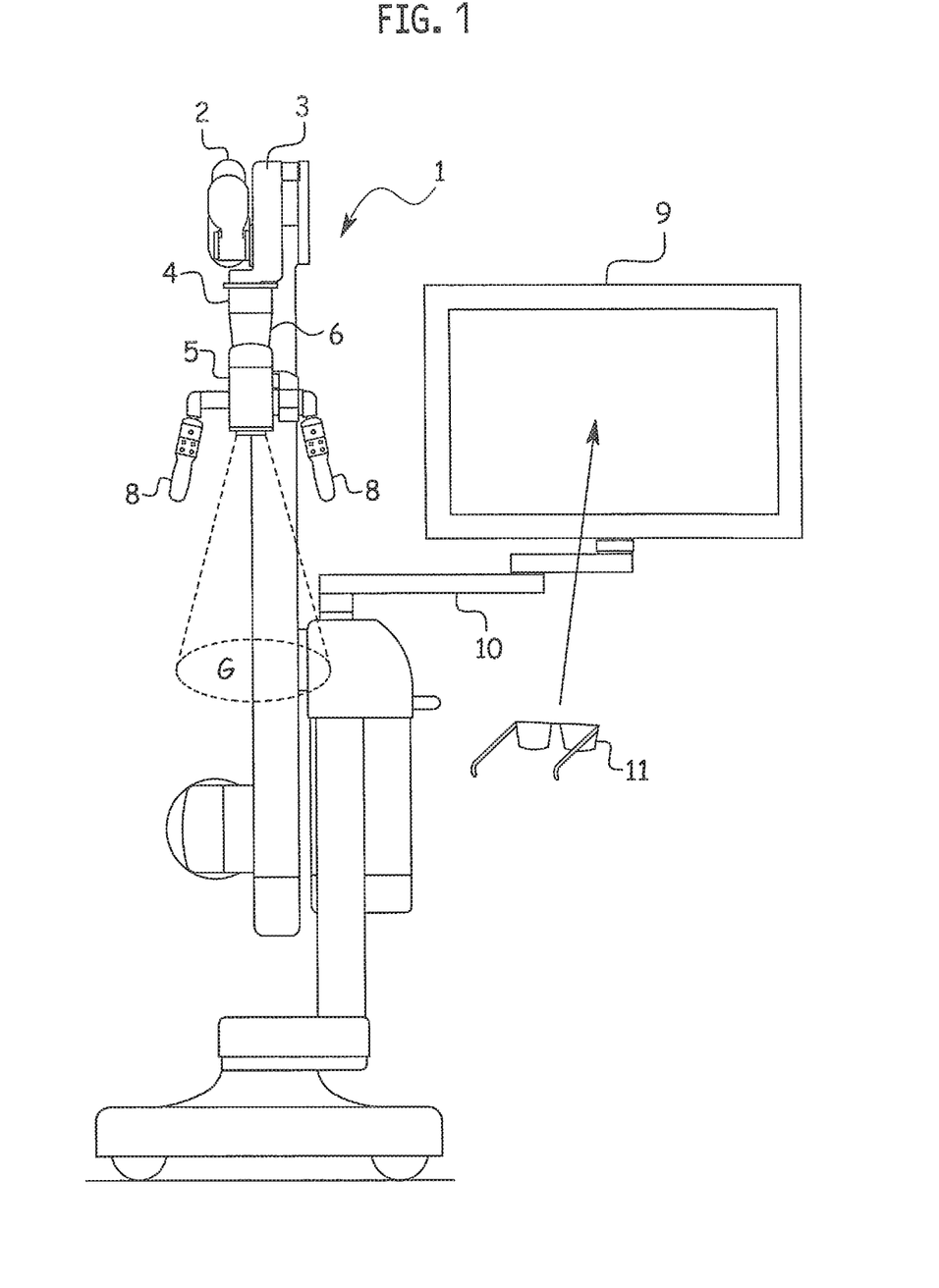
FIG. 1 is a front view illustrating a surgical stereoscopic observation apparatus according to an embodiment of the present invention.
Figure 2:
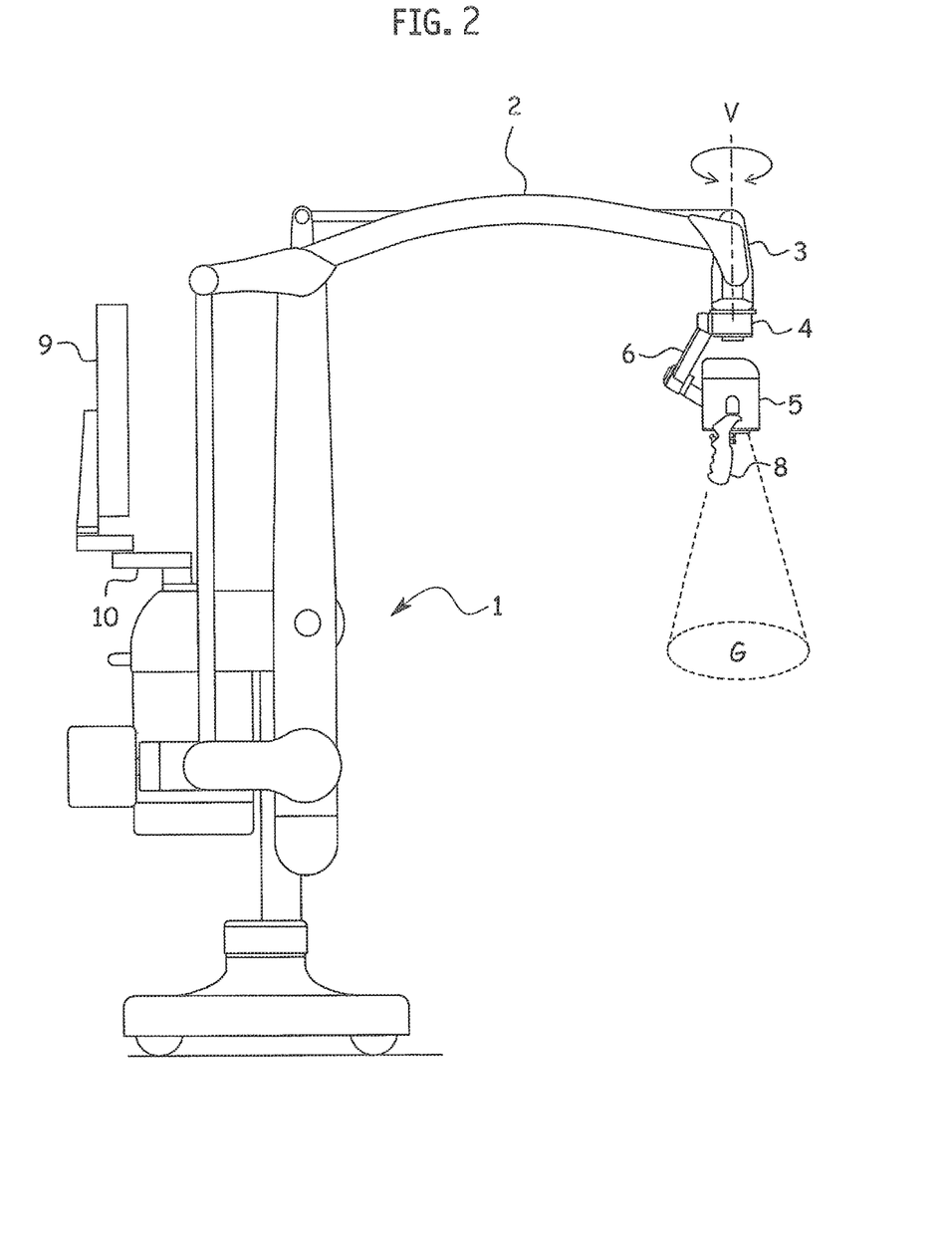
FIG. 2 is a side view illustrating the apparatus.

The surgical stereoscopic observation apparatus has a stand 1 that has a support arm 2 extending laterally from the stand 1. The support arm 2 has a parallel linkage structure that keeps a position of a front link 3 of the support arm 2 vertical even when the support arm 2 is moved upward or downward. The front link 3 corresponds to a front vertical side of the parallel linkage structure of the support arm 2 and has a virtual vertical axis V. A lower end of the front link 3 supports a front member 4 that is turnable with respect to the front link 3 around the vertical axis V. The front member 4 has an auxiliary arm 6 that supports a camera 5. The camera 5 is able to change the direction thereof around a horizontal axis H and slant axis S of the auxiliary arm 6. The camera 5 is able to stereoscopically take optical images having binocular parallax of an operative field G.

Figure 3:
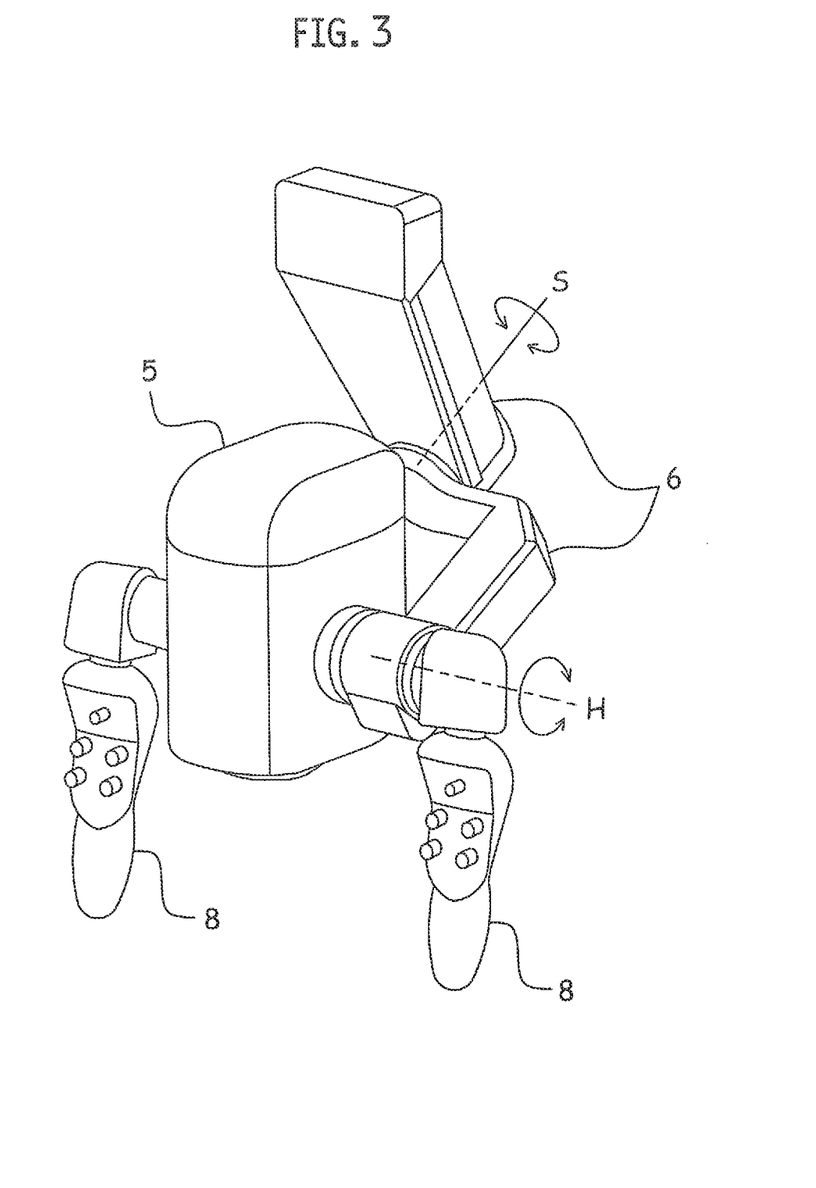
FIG. 3 is a perspective view illustrating a camera of the apparatus.

The camera 5 has a control grip 8 on each side thereof. An operator grasps the grips 8 to move the camera 5 together with the stand 1 to an optional location, or change a spatial position of the camera 5, or orient the camera 5 to an optional direction.

The stand 1 has a folding arm 10 that supports an electronic image display unit 9. The display unit 9 may be a liquid-crystal panel or an organic EL display (OLED) that receives signals from the camera 5, synthesizes the signals in real time to form a pair of electronic images having binocular parallax, and displays the images. The operator or an assistant may employ special glasses 11 to stereoscopically observe the images displayed on the display unit 9.

Figure 4:
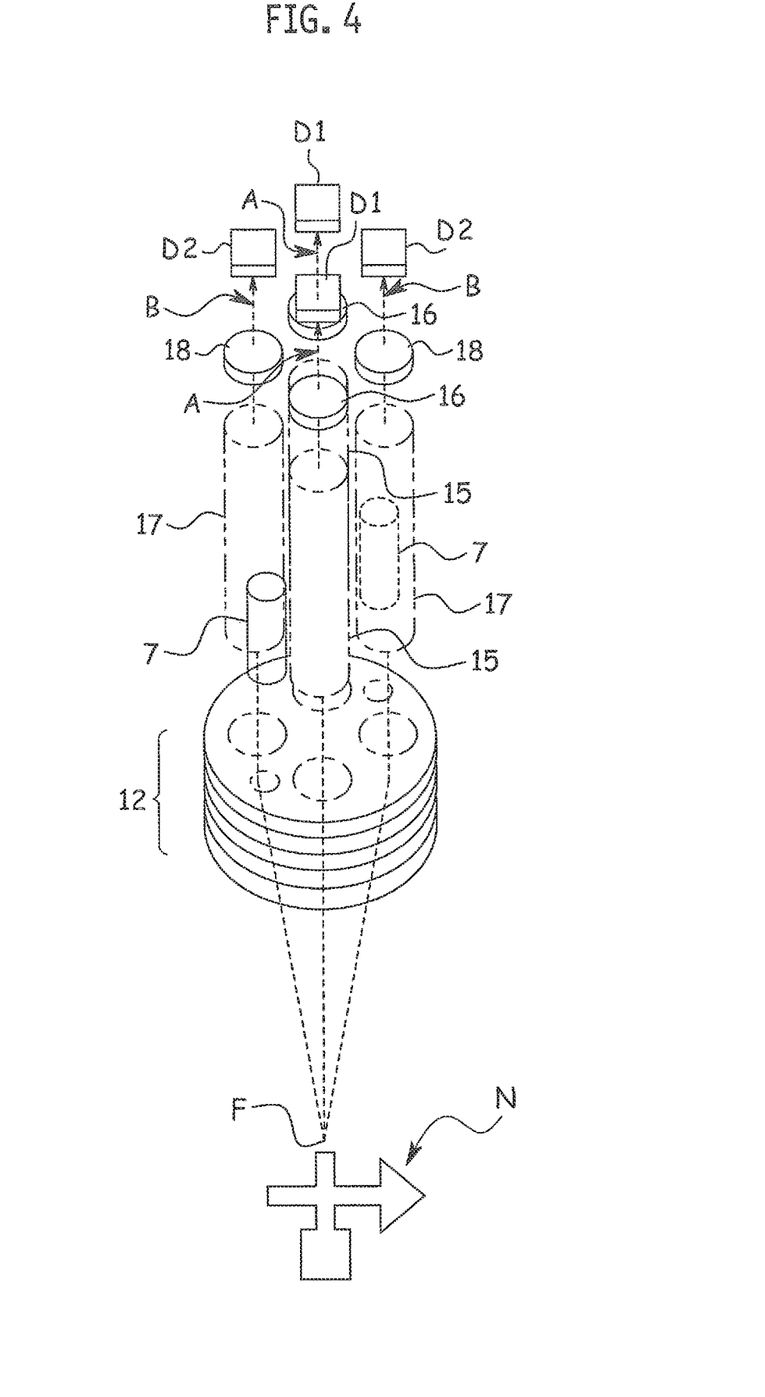
FIG. 4 is a perspective view illustrating an internal structure of the camera.

An internal structure of the camera 5 will be explained.

Figure 5:
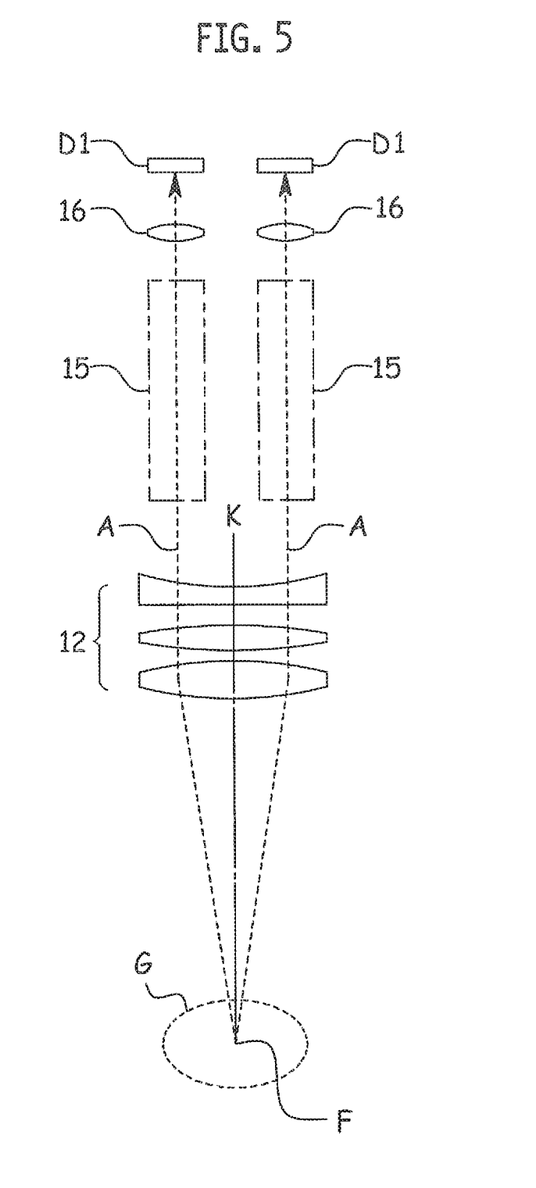
FIG. 5 is a front view illustrating main optical paths defined inside the camera.

The camera 5 has a stereoscopic observation enabling structure. Defined inside the camera 5 are left and right main optical paths A of light flux radiated from the field G. Arranged at a lower part of the camera 5 is an objective optical system 12.

Arranged adjacent to the objective optical system 12 is a douser 13 behind which an illuminating unit 14 is arranged inside the camera 5. The illuminating unit 14 emits illuminating light E toward the operative field G. Since the illuminating unit 14 is incorporated in the camera 5, there is no need of arranging an optical cable to introduce external illuminating light. Such an optical cable is rigid and heavy to hinder the movement of the camera 5 if it is arranged on or around the camera 5. The embodiment causes no such a problem because it has no need of arranging the optical cable for guiding illuminating light.

Arranged above the objective optical system 12 within the range thereof are a pair of variable power optical systems 15. Two optical axes of the variable power optical systems 15 are aligned in a direction L-R of the operator. The main optical paths A pass through the objective optical system 12, the two variable power optical systems 15, and imaging lenses 16 and reach imaging elements D1. The imaging elements D1 (D2) are, for example, CCD area image sensors.

Figure 6:
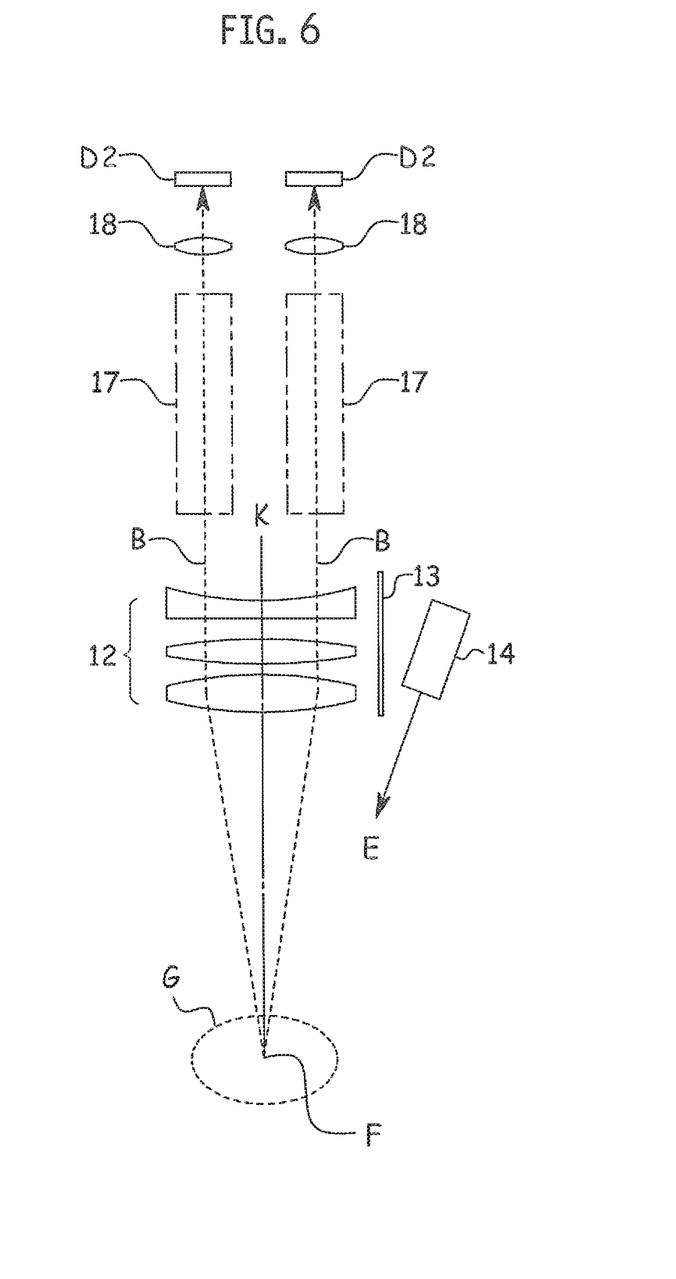
FIG. 6 is a side view illustrating secondary optical paths defined inside the camera.

Also arranged above the objective optical system 12 within the range thereof are a pair of variable power optical systems 17 whose optical axes are independent of those of the variable power optical systems 15. Two optical axes of the variable power optical systems 17 are aligned in a direction F-C of the operator. The aligning direction F-C of the optical axes of the variable power optical systems 17 is orthogonal to the aligning direction L-R of the optical axes of the variable power optical systems 15. Optical paths passing through the variable power optical systems 17 are secondary optical paths B of light flux radiated from the field G. The secondary optical paths B pass through imaging lenses 18 and reach imaging elements D2. An aligning direction of the secondary optical paths B differs by 90 degrees from an aligning direction of the main optical paths A.

Figure 7:
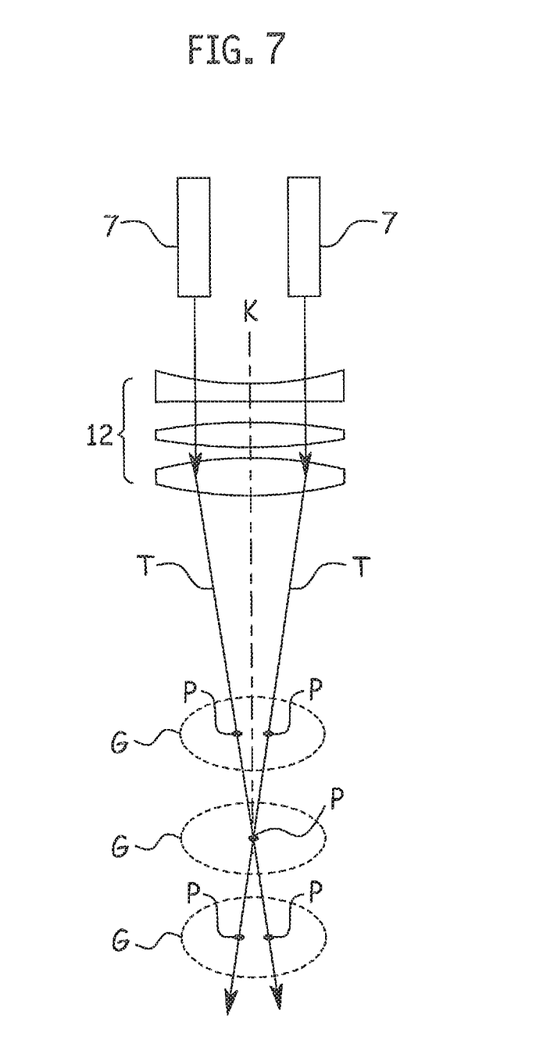
FIG. 7 is a view illustrating focusing beam emitters installed in the camera.

A pair of focusing beam emitters 7 are arranged inside the camera 5 above the objective optical system 12 at positions outside the variable power optical systems 15 and 17 so that the focusing beam emitters 7 never interfere with the variable power optical systems 15 and 17.

Each of the focusing beam emitters 7 is a small semiconductor laser emitter that emits a semiconductor laser focusing beam T along an optical axis K. According to the embodiment, the optical axis K agrees with the optical axis of the objective optical system 12. Namely, the main optical paths A, secondary optical paths B, and optical paths of the focusing beams T are within the objective optical system 12 and are defined in parallel with the optical axis K so that the optical paths never interfere with one another. Beams advancing along the main and secondary optical paths A and B and the focusing beams T are iii parallel with the optical axis K and pass through the objective optical system 12 and a focal point F. Namely, the focusing beams T pass through the objective optical system 12 and converge at a point of focal length of the objective optical system 12. Even if the focal length of the objective optical system 12 is changed, the focusing beams T always converge at the focal point F along with the change.

The focusing beam emitters 7 are linked through a controller (not illustrated) to control buttons on the control grips 8. While the control buttons are being pressed, the focusing beam emitters 7 emit the focusing beams T. The control buttons on the control grips 8 are pressed to, for example, release electromagnetic clutches of movable parts of the stand 1 and change the focal length of the objective optical system 12.

Figure 8:
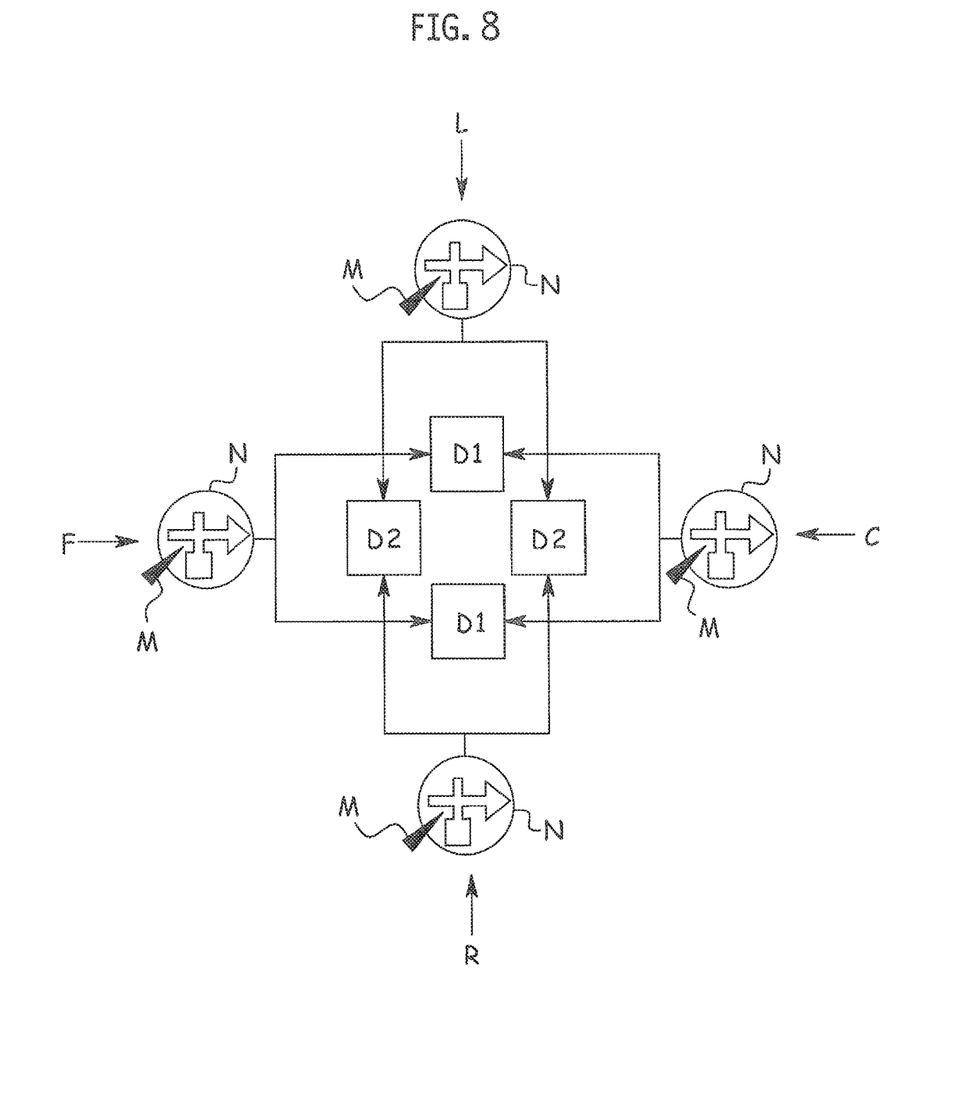
FIG. 8 is an explanatory view illustrating relationships between imaging elements installed in the camera and observation directions.

According to the embodiment, the main and secondary optical paths A and B are aligned in directions differing by 90 degrees from each other and pass through the single objective optical system 12, to form images on the imaging elements D1 and D2, respectively. FIG. 8 illustrates relationships between the imaging elements D1 and D2 and observation directions. When electronic images provided by the imaging elements D1 on the main optical paths A are displayed as they are on the display unit 9, there is provided a stereoscopic image for the operator who faces a direction F. A circle N in FIG. 8 corresponds to a view field and includes a symbol having a special shape to clarify an orientation. A black triangle M at the circle N is a surgical instrument inserted from the near right side of the operator into the view field. When the electronic images from the imaging elements D1 are turned by 180 degrees (i.e., inverted front-rear-wise and left-right-wise) and displayed on the display unit 9, there is provided a stereoscopic image for an assistant who faces a direction C opposite to the operator. At this time, an electronic image for the right eye of the operator who faces the direction F corresponds to that for the left eye of the assistant who faces the direction C. Similarly, an electronic image for the left eye facing the direction F corresponds to that for the right eye facing the direction C.

When electronic images provided by the imaging elements D2 on the secondary optical paths B are displayed as they are on the display unit 9, there is provided a stereoscopic image for an assistant who is at a 90-degree right position of the operator and faces a direction R. When the electronic images from the imaging elements D2 are inverted front-rear-wise and left-right-wise, there is provided a stereoscopic image for an assistant who is at a 90-degree left position of the operator and faces a direction L. In this way, the embodiment is able to display stereoscopic images not only for an operator and an assistant positioned opposite to the operator but also for assistants positioned on the left and right sides of the operator, so that the operator and assistants may easily conduct a cooperative operation. Namely, the present embodiment allows the operator and assistants to observe images of the operative field G as if they are directly observing the operative field G from their respective positions.

When the operator presses the control buttons on the control grips 8 to, for example, move the camera 5, the focusing beam emitters 7 emit the focusing beams T while the buttons are being pressed. When the camera 5 is moved to a required position on the operative field G, the focusing beams T form spots P on the operative field G. The spots P on the operative field G are visible to the naked eye and observable on the display unit 9.

At this time, the spots P converge into one on the operative field G if the focal point F of the objective optical system 12 is correctly on the operative field G as illustrated in FIG. 7. On the other hand, if the focal point F disagrees with the operative field G, the two spots P are discretely observed on the operative field G and a distance between the two spots P is proportional to a deviation from the focal point F. If the distance between the two spots P is large, the deviation from the focal point F is large, and if the distance is small, the deviation is small.

Whenever moving the stand 1 and camera 5 or changing the focal length of the objective optical system 12 by pressing the control buttons on the control grips 8, the operator is able to easily observe the spots P of the focusing beams T with the naked eye or on the display unit 9 and quickly determine whether or not the focal point F of the objective optical system 12 is on the operative field G.

According to the present embodiment, images displayed on the display unit 9 such as a liquid-crystal display panel are three-dimensionally observed through the special glasses 11. Instead, the images may be displayed on a pair of left and right display panels incorporated in a 3D viewer and may stereoscopically be observed through left and right eyepieces of the 3D viewer.

In summary, the first aspect of the present invention arranges, in addition to a pair of the main optical paths, a pair of the secondary optical paths that are aligned in a direction differing by 90 degrees from an aligning direction of the main optical paths. For the main and secondary optical paths, the first aspect arranges the imaging elements, respectively, to provide stereoscopic electronic images oriented not only in the directions of an operator and an assistant positioned opposite to the operator but also in the directions of assistants positioned on the 90-degree left and right sides of the operator, thereby allowing the operator and assistants to easily conduct a cooperative operation.

The second aspect of the present invention arranges the illuminating unit inside the camera, to eliminate the need of arranging an optical cable for guiding external illuminating light, thereby allowing the camera to freely move without restrictions by such an optical cable.

The third aspect of the present invention arranges the focusing beam emitters to emit two focusing beams in parallel with the optical axis of the objective optical system. The two focusing beams converge into a single spot on an operative field if the focal point of the objective optical system is correctly on the operative field. If the focal point disagrees with the operative field, the two focusing beams form two discrete spots on the operative field. With the naked eye or on the display unit, the operator is able to observe the spots formed by the two focusing beams on the operative field and quickly determine whether or not the focal point of the objective optical system is on the operative field. While observing the state of the spots of the focusing beams on the operative field, the operator vertically moves the camera to converge the two spots into one, thereby easily focusing the objective optical system with respect to the operative field.

The fourth aspect of the present invention makes the two focusing beams enter the objective optical system at locations that are different from locations where beams for the variable power optical systems exit from the objective optical system. The fourth aspect avoids interference between the focusing beams and the beams for the variable power optical systems, thereby securing incidence positions for the focusing beams on the objective optical system.

This patent application claims the benefit of priority under 35 U.S.C. 119(a) to Japanese Patent Applications No. 2015-158686 filed on Aug. 11, 2015 and No. 2015-220895 filed on Nov. 11, 2015 whose disclosed contents are cited herein.

What is claimed is:

1. A surgical stereoscopic observation apparatus comprising: a camera including:
    two main optical paths defined within the a range of light flux passed through an objective optical system and guiding a pair of first beams from the objective optical system to a pair of first imaging elements through a pair of first variable power optical systems; and
    two secondary optical paths defined within the range of light flux passed through the objective optical system and aligned in a direction differing by 90 degrees from an aligning direction of the main optical paths, and guiding a pair of second beams from the objective optical system to a pair of second imaging elements through a pair of second variable power optical systems; and
    a display displaying electronic images taken by the camera, orientations of the electronic images differing by 90 degrees from one another,
    wherein the pair of first variable power optical systems and the pair of second variable power optical systems are each within the objective optical system, parallel to an optical axis of the objective optical system, orthogonally aligned about the optical axis, and do not interfere with one another.

2. The surgical stereoscopic observation apparatus of claim 1, wherein the camera includes a light emitter.

3. The surgical stereoscopic observation apparatus of claim 1, wherein
    the camera includes two focusing beam emitters wherein each emits focusing beams toward the objective optical system in parallel with the optical axis of the objective optical system, and
    the two focusing beams converge at a point of focal length of the objective optical system.

4. The surgical stereoscopic observation apparatus of claim 3, wherein the two focusing beams enter the objective optical system at locations that are different from locations where the pairs of the first and second beams for the first and second variable power optical systems exit from the objective optical system.

* * * * *

UNITED STATES PATENT AND TRADEMARK OFFICE
CERTIFICATE OF CORRECTION

| | |
|---|---|
| PATENT NO. | : 10,122,991 B2 |
| APPLICATION NO. | : 15/229375 |
| DATED | : November 6, 2018 |
| INVENTOR(S) | : Nakamura |

Page 1 of 1

It is certified that error appears in the above-identified patent and that said Letters Patent is hereby corrected as shown below:

In the Claims

Column 6, Line 12 (Claim 1) please change "the a range" to --a range--

Signed and Sealed this
Sixteenth Day of April, 2019

Andrei Iancu
*Director of the United States Patent and Trademark Office*